United States Patent [19]
Bok et al.

[11] Patent Number: 5,763,414
[45] Date of Patent: Jun. 9, 1998

[54] HESPERIDIN AND HESPERETIN AS 3-HYDROXY-3-METHYLGLUTARYL COA (HMG-COA) REDUCTASE INHIBITOR

[75] Inventors: Song-Hae Bok; Kwang-Hee Son; Tae-Sook Jeong; Byoung-Mog Kwon; Young-Kook Kim; Doil Choi; Sung-Uk Kim; Ki-Hwan Bae, all of Daejeon; Yong-Bok Park; Myung-Sook Choi, both of Daegu; Ingyu Hwang, Daejeon; Surk-Sik Moon, Gongju-shi; Yong-Kook Kwon, Daejeon; Jung-Ah Ahn, Daejeon; Eun-Sook Lee, Daejeon, all of Rep. of Korea

[73] Assignee: Korea Institute of Science and Technology, Seoul, Rep. of Korea

[21] Appl. No.: 949,669

[22] Filed: Oct. 14, 1997

[30] Foreign Application Priority Data

Oct. 14, 1996 [KR] Rep. of Korea ................ 1996-45735

[51] Int. Cl.$^6$ .......................... A61K 31/70; A61K 31/35
[52] U.S. Cl. .......................................... 514/27; 514/456
[58] Field of Search ........................................ 514/27, 456

[56] References Cited

PUBLICATIONS

Caplus abstract No. 123:275688, Monforte et al., 1995.

Caplus abstract No. 126:26860, Yanagida et al., 1996.

*Primary Examiner*—Raymond Henley, III
*Attorney, Agent, or Firm*—Anderson Kill & Olick, P.C.

[57] ABSTRACT

A method for inhibiting the activity of 3-hydroxy-3-methylglutaryl CoA(HMG-CoA) reductase in mammals comprises administering hesperidin or hesperetin thereto.

6 Claims, No Drawings

HESPERIDIN AND HESPERETIN AS 3-HYDROXY-3-METHYLGLUTARYL COA (HMG-COA) REDUCTASE INHIBITOR

FIELD OF THE INVENTION

The present invention relates to a method for inhibiting the activity of 3-hydroxy-3-methylglutaryl CoA(HMG-CoA) reductase in a mammal which comprises administering hesperidin or hesperetin thereto.

BACKGROUND OF THE INVENTION

In recent years, coronary cardio-circulary diseases, e.g., atherosclerosis and hypercholesterolemia, have increasingly become a major cause of deaths. It has been reported that an elevated plasma cholesterol level causes the deposition of fat, macrophages and foam cells on the wall of blood vessels, such deposit leading to plaque formation and then to atherosclerosis(Ross, R., Nature, 362, 801–809(1993)). One of the methods for decreasing the plasma cholesterol level is alimentotherapy to reduce the ingestion of cholesterol and lipids. Another method is to lower the rate of cholesterol biosynthesis which takes place in the liver. It has been reported that hypercholesterolemia can be treated effectively by reducing the rate of cholesterol biosynthesis through the inhibition of HMG-CoA reductase which mediates the synthesis of mevalonic acid, an intermediate in the biosynthesis of sterols or isoprenoids(Cardiovascular Pharmacology, William W. Parmley and Kanu Chatterjee Ed., Wolfe Publishing, pages 8.6–8.7, 1994).

Therefore, numerous efforts have been made to develop medicines to inhibit HMG-CoA reductase; and, as a result, several compounds derived from Penicillium sp. and Aspergillus sp. have been commercialized. Specifically, Lovastatin® and Simvastatin® developed by Merck Co., U.S.A., and Pravastatin® developed by Sankyo Co., Japan, have been commercialized(C. D. R. Dunn, Stroke: Trends, Treatment and Markets, SCRIPT Report, PJB Publications Ltd., 1995). However, these medicines are very expensive and a long-term administration thereof is known to induce an adverse side effect of increasing creatine kinase in the liver. Accordingly, there has continued to exist a need to develop an inexpensive and non-toxic inhibitor of HMG-CoA reductase.

Hesperidin and the aglycon of hesperidin, hesperetin, are flavonoids found in lemons, grapefruits, tangerines and oranges(Citrus sinensis) and they have the following structures(Horowitz, Gentili, Tetrahedron, 19, 773(1943)):

Hesperidin has been used for the prevention and treatment of cerebral anemia, retinal hemorrhage and pelioma. However, there has been no report on the HMG-CoA reductase inhibitory activity of hesperidin or hesperetin.

SUMMARY OF THE INVENTION

Accordingly, it is a primary object of the present invention to provide a method for inhibiting the HMG-CoA reductase activity in mammals.

In accordance with one aspect of the present invention, there is provided a method for inhibiting the HMG-CoA reductase activity in mammals which comprises administering hesperidin or hesperetin thereto.

DETAILED DESCRIPTION OF THE INVENTION

The method of the present invention for inhibiting the activity of HMG-CoA in mammals comprises administering hesperidin or hesperetin thereto.

Hesperidin and hesperetin may be extracted from the peel of citrus or synthesized according to the process described by Zemplen, Bognar, Ber., 75, 1043(1943) and Seka, Prosche, Monatsh., 69, 284(1936). Further, hesperetin can be prepared by the hydrolysis of hesperidin.

Hesperidin or hesperetin exerts an inhibitory effect on the HMG-CoA reductase at a dose of 0.5 mg/kg/day or more, the inhibitory effect increasing with the dose thereof.

Moreover, in spite of their potent efficacies, hesperidin and hesperetin show little toxicity or mitogenicity in tests using mice. More specifically, hesperidin exhibits no toxicity when it is orally administered to a mouse at a dosage of 1,000 mg/kg, which corresponds to oral administration dose of 50 to 100 g/kg body weight of hesperidin for a person weighing 50 kg. Further, hesperidin and hesperetin exert no adverse effects on the liver function.

The present invention also provides a pharmaceutical composition for inhibiting the HMG-CoA reductase activity, which comprises hesperidin or hesperetin as an active ingredient, in combination with pharmaceutically acceptable excipients, carriers or diluents.

A pharmaceutical formulation may be prepared by using the composition in accordance with any of the conventional procedures. In preparing the formulation, the active ingredient is preferably admixed or diluted with a carrier, or

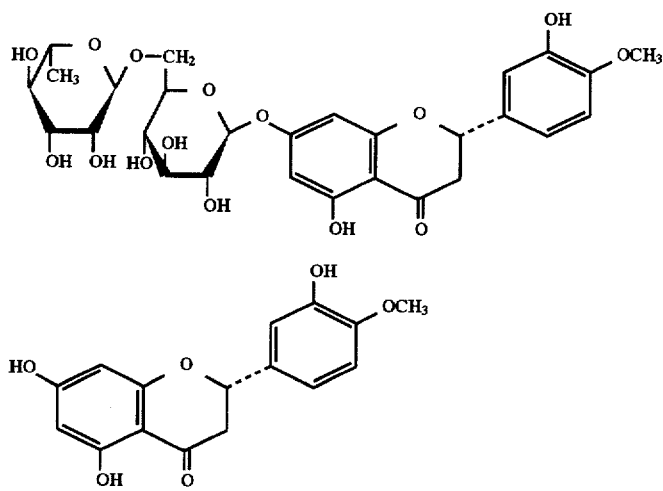

Hesperidin

Hesperetin enclosed within a carrier which may be in the form of a capsule, sachet or other container. When the carrier serves as a diluent, it may be a solid, semi-solid or liquid material acting as a vehicle, excipient or medium for the active ingredient. Thus, the formulations may be in the form of a tablet, pill, powder, sachet, elixir, suspension, emulsion, solution, syrup, aerosol, soft and hard gelatin capsule, sterile injectable solution, sterile packaged powder and the like.

Examples of suitable carriers, excipients, and diluents are lactose, dextrose, sucrose, sorbitol, mannitol, starches, gum acacia, alginates, gelatin, calcium phosphate, calcium silicate, cellulose, methyl cellulose, microcrystalline cellulose, polyvinylpyrrolidone, water, methylhydroxybenzoates, propylhydroxybenzoates, talc, magnesium stearate and mineral oil. The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a mammal by employing any of the procedures well known in the art.

The pharmaceutical formulation of the present invention can be administered via various routes including oral, transdermal, subcutaneous, intravenous and intramuscular introduction. In case of human, a typical daily dose of hesperidin or hesperetin may range from about 0.5 to 300 mg/kg body weight, preferably 5 to 30 mg/kg body weight, and can be administered in a single dose or in divided doses. However, it should be understood that the amount of the active ingredient actually administered ought to be determined in light of various relevant factors including the condition to be treated, the chosen route of administration, the age, sex and body weight of the individual patient, and the severity of the patient's symptom; and, therefore, the above dose should not be intended to limit the scope of the invention in any way.

Moreover, hesperidin and hesperetin can be incorporated in foods or beverages for the purpose of inhibiting the HMG-CoA reductase activity.

As described above, hesperidin or hesperetin can be used as an effective, non-toxic pharmaceutical agent for inhibiting HMG-CoA reductase activity.

The following Examples are intended to further illustrate the present invention without limiting its scope.

Further, percentages given below for solid in solid mixture, liquid in liquid, and solid in liquid are on a wt/wt, vol/vol and wt/vol basis, respectively, and all the reactions were carried out at room temperature, unless specifically indicated otherwise.

EXAMPLE 1

Administration of Hesperidin and Hesperetin to an Animal 24 four-week-old Sprague-Dawley rats(Taihan laboratory animal center, Korea) each weighing about 90 to 110 g were evenly divided into three dietary groups by a randomized block design. The rats of the three groups were fed with three different high-cholesterol diets, i.e., AIN-76 laboratory animal diet(ICN Biochemicals, Cleveland, Ohio, U.S.A.) containing 1% cholesterol(Control group), 1% cholesterol plus 0.1% hesperidin(Hesperidin group), and 1% cholesterol plus 0.1% hesperetin(Hesperetin group), respectively. The compositions of diets fed to the three groups are shown in Table I.

TABLE I

| | Dietary group | | |
|---|---|---|---|
| Component | Control group | Hesperidin group | Hesperetin group |
| Casein | 20 | 20 | 20 |
| D,L-methionine | 0.3 | 0.3 | 0.3 |
| Corn starch | 15 | 15 | 15 |
| Sucrose | 49 | 48.9 | 48.9 |
| Cellulose powder[*1] | 5 | 5 | 5 |
| Mineral mixture[*1] | 3.5 | 3.5 | 3.5 |
| Vitamin mixture[*1] | 1 | 1 | 1 |
| Choline citrate | 0.2 | 0.2 | 0.2 |
| Corn oil | 5 | 5 | 5 |
| Cholesterol | 1 | 1 | 1 |
| Hesperidin[*2] | | 0.1 | |
| Hesperetin[*2] | | | 0.1 |
| Total | 100 | 100 | 100 |

[*1]: Purchased from TEKLAD Premier Co. (Madison, WI, U.S.A.).
[*2]: Purchased from Sigma Chemical Company (St. Louis, Mo., U.S.A)

The rats were allowed to feed freely on the specified diet together with water for six weeks, the ingestion amount was recorded daily and the rats were weighed every 7 days, and then the record was analyzed. All rats showed a normal growth rate and there was observed no significant difference among the three groups in terms of the feed ingestion amount and the weight gain.

EXAMPLE 2

Determination of Total Cholesterol, HDL-cholesterol and Neutral Lipid Content in plasma The effect of administering hesperidin and hesperetin to rats on the plasma cholesterol and neutral lipid content was determined as follows.

Blood samples were taken from the rats of the three dietary groups and plasma HDL fractions were separated therefrom by using HDL-cholesterol reagent(Sigma Chemical Co., Cat. No. 352-3) containing dextran-sulfate. Total cholesterol and HDL-cholesterol levels were determined by using Sigma Diagnostic Kit Cat. No. 352-100(Sigma Chemical Co., U.S.A.)(Allain et al., Clin. Chem., 20, 470–475 (1974)). Neutral lipids level was determined by using Sigma Diagnostic Kit Cat. No. 339-50(Bucolo, G. and David, H., Clin. Chem., 19, 476–482(1973)). The result is shown in Table II, wherein the total plasma cholesterol level decreased by 11% in the hesperidin-fed rat group and by 15% in the hesperetin-fed rat group, as compared with that of the control group.

TABLE II

| | Group | | |
|---|---|---|---|
| Lipids Conc. | Control group | Hesperidin group | Hesperetin group |
| Total-C (mg/dl) | 147.8 ± 34.8 | 131.6 ± 29.7 | 125.1 ± 15.6 |
| HDL-C (mg/dl) | 22.2 | 18.7 | 25.7 |
| $\frac{\text{HDL-C}}{\text{Total-C}}$ (%) | 15.7 ± 5.3 | 15 ± 4.9 | 20 ± 5.6 |
| Total-C TG (mg/dl) | 99.2 ± 18.9 | 92.7 ± 20.5 | 114.6 ± 18.8 |

* Total-C: Total-cholesterol
* HDL-C: HDL-cholesterol
* TG: Triglyceride

EXAMPLE 3

Activity of Hesperidin and Hesperetin in HMG-CoA Reductase Inhibition (Step 1) Preparation of microsomes To determine the effect of hesperidin and hesperetin feeding to rats on the activity of HMG-CoA reductase, a regulatory enzyme of the cholesterol synthesis in the liver, microsomes were separated from the liver tissue to be used as an enzyme source.

First, the rats of the three groups were sacrificed by decapitation and the livers were excised and immediately placed in an ice-cold homogenization medium(50 mM $KH_2PO_4$(pH 7.0), 0.2M sucrose, 2 nM dithiothreitol(DTT)). The livers were homogenized in the homogenization medium(2 ml medium/g of the liver) with a Waring blendor for 15 sec.(three strokes with a motor-driven Teflon pestle in a Potter-Elvehjem type glass homogenizer). The homogenate was centrifuged at 15,000×g for 10 min. and the supernatant thus obtained was centrifuged at 100,000×g for 75 min. to obtain microsomal pellets, which were then resuspended in the homogenization medium containing 50 mM EDTA and centrifuged at 100,000×g for 60 min. The supernatant containing the microsome was used as an enzyme source.

(Step 2) HMG-CoA reductase assay

The activity of HMG-CoA reductase was determined by employing [$^{14}$C]HMG-CoA, in accordance with the method of Shapiro et al.(*Biochemica et Biophysica Acta*, 370, 369-377(1974)) as follows.

The enzyme in the supernatant containing the microsome obtained in (Step 1) was activated at 37° C. for 30 min. Added to a reaction tube were 20 µl of HMG-CoA reductase assay buffer(0.25M $KH_2PO_4$(pH 7.0), 8.75 mM EDTA, 25 mM DTT, 0.45M KCl and 0.25 mg/ml BSA), 5 µl of 50 mM NADPH, 5 µl of [$^{14}$C]HMG-CoA(0.05 µCi/tube, final conc. 120 µM), and 10 µl of activated microsomal enzyme (0.03-0.04 mg), and the mixture was incubated at 37° C. for 30 min. The reaction was terminated by adding 10 µl of 6M HCl to the mixture, and the mixture was incubated at 37° C. for 15 min. to allow complete lactonization of the product (mevalonate). The precipitate was removed by centrifugation at 10,000×g for 1 min. and the supernatant was applied to a Silica gel 60G TLC plate(Altech, Inc., Newark, U.S.A.) and then developed with benzene:acetone(1:1, v/v). A region having a Rf value ranging from 0.65 to 0.75 was removed by scraping with a disposable cover slips and assayed for radioactivity with 1450 Microbeta liquid scintillation counter(Wallacoy, Finland). Enzyme activities were calculated as picomoles mevalonic acid synthesized per min. per mg protein(pmoles/min/mg protein). The result is shown in Table III.

TABLE III

| | Group | | |
|---|---|---|---|
| | Control group | Hesperidin group | Hesperetin group |
| HMG-CoA reductase activity (pmole/min/mg protein | 147 ± 12.5 | 112.1 ± 12.8 | 118.5 ± 114.3 |

As can be seen from Table III, the control group rats showed a relatively high HMG-CoA reductase activity, while the HMG-CoA activities observed with the hesperidin-fed rat group and the hesperetin-fed rat group are lower than that of the control group by 24% and 19%, respectively.

EXAMPLE 4

Toxicity of Orally Administered Hesperidin 7 to 8 week-old, specific pathogen-free ICR female mice(8 heads) each weighing about 25 to 29 g and male mice(8 heads) each weighing about 34 to 38 g were bred under a condition of temperature 22±1° C., moisture 55±5% and photoperiod 12L/12D. Fodder(Cheiljedang Co., mouse and rat fodder) and water were sterilized and fed to the mice.

Hesperidin was dissolved in 0.5% Tween 80 to a concentration of 100 mg/ml, and the solution was orally administered to the mice in an amount of 0.2 ml per 20 g of mouse body weight. The solution was administered once and the mice were observed for 10 days for signs of adverse effects or death according to the following schedule: 1, 4, 8, and 12 hours after the administration and, every 12 hours thereafter. The weight changes of the mice were recorded every day to examine the effect of hesperidin. Further, on the 10th day, the mice were sacrificed and the internal organs were visually examined.

All the mice were alive at day 10 and hesperidin showed no toxicity at a dose of 1,000 mg/kg. The autopsy revealed that the mice did not develop any pathological abnormality, and no weight loss was observed during the 10 day test period. Accordingly, it was concluded that hesperidin is not toxic when orally administered to an animal.

The following Formulation Example is for illustration only and not intended to limit the scope of the invention in any way.

Formulation Example

Hard gelatin capsules were prepared using the following ingredients:

| | Quantity (mg/capsule) |
|---|---|
| Active ingredient (hesperidin) | 20 |
| Starch, dried | 160 |
| Magnesium stearate | 20 |
| Total | 200 mg |

While the invention has been described with respect to the above specific embodiments, it should be recognized that various modifications and changes may be made to the invention by those skilled in the art which also fall within the scope of the invention as defined by the appended claims.

What is claimed is:

1. A method for inhibiting the activity of 3-hydroxy-3-methylglutaryl CoA(HMG-CoA) reductase in a mammal which comprises administering an effective amount of hesperidin or hesperetin thereto.

2. The method of claim 1, wherein the mammal is human.

3. The method of claim 2, wherein the effective amount of hesperidin ranges from 0.5 to 300 mg/kg body weight/day.

4. The method of claim 2, wherein the effective amount of hesperetin ranges from 0.5 to 300 mg/kg body weight/day.

5. The method of claim 1, wherein said hesperidin or hesperetin is administered in the form of a pharmaceutical composition.

6. The method of claim 1, wherein said hesperidin or hesperetin is administered in the form of an additive or a dietary supplement in food or beverage.

* * * * *

UNITED STATES PATENT AND TRADEMARK OFFICE
CERTIFICATE OF CORRECTION

PATENT NO. : 5,763,414
DATED : June 9, 1998
INVENTOR(S) : Song-Hae Bok, et al

It is certified that error appears in the above-indentified patent and that said Letters Patent is hereby corrected as shown below:

On the title page, item [30] Foreign Application Priority Data

Oct. 14, 1996   [KR]   Rep. of Korea   96-45735

Signed and Sealed this

Eighteenth Day of August, 1998

Attest:

BRUCE LEHMAN

*Attesting Officer*    *Commissioner of Patents and Trademarks*